United States Patent [19]

Isaacs et al.

[11] Patent Number: 5,434,182
[45] Date of Patent: Jul. 18, 1995

[54] ANTIBACTERIAL FATTY ACID COMPOSITIONS

[76] Inventors: Charles E. Isaacs, 30 Devon Dr. North, Manalapan, N.J. 07726; Kwang S. Kim, 178 Dahlia St., Staten Island, N.Y. 10312; Halldor Thormar, Langagerdi 15, Reykjavik, Iceland; William C. Heird, 2001 Holcombe Blvd., Apt. 2701, Houston, Tex. 77030; Henryk M. Wisniewski, 141 Nixon Ave., Staten Island, N.Y. 10304

[21] Appl. No.: 58,056

[22] Filed: May 3, 1993

Related U.S. Application Data

[63] Continuation of Ser. No. 896,120, Jun. 10, 1992, abandoned, which is a continuation-in-part of Ser. No. 543,111, Jun. 25, 1990, which is a continuation-in-part of Ser. No. 365,291, Jun. 12, 1989, which is a continuation-in-part of Ser. No. 140,078, Dec. 31, 1987, Pat. No. 4,997,851.

[51] Int. Cl.⁶ .................. A61K 31/22; A61K 31/225; A61K 31/20
[52] U.S. Cl. .................. 514/546; 514/547; 514/558
[58] Field of Search .............. 514/546, 547, 549, 552, 514/557, 558

[56] References Cited

U.S. PATENT DOCUMENTS

| | | | |
|---|---|---|---|
| Re. 32,990 | 7/1989 | Kinsolving | 514/560 |
| 4,223,041 | 9/1980 | Carroll | 424/322 |
| 4,489,097 | 12/1984 | Stone | 514/557 |
| 4,513,008 | 4/1985 | Revici et al. | 514/703 |
| 4,613,501 | 9/1986 | Horowitz | 424/89 |
| 4,767,788 | 8/1988 | Diana | 514/574 |
| 4,806,352 | 2/1989 | Cantrell | 514/937 |
| 4,828,912 | 5/1989 | Hossain | 428/289 |
| 4,841,023 | 6/1989 | Horowitz | 530/351 |
| 4,853,978 | 8/1989 | Stockum | 2/167 |
| 4,897,304 | 1/1989 | Hossain | 428/289 |

FOREIGN PATENT DOCUMENTS

| | | |
|---|---|---|
| 21504 | 1/1981 | European Pat. Off. |
| 0068552 | 1/1983 | European Pat. Off. |
| 289204 | 11/1988 | European Pat. Off. |
| 57-106618 | 7/1982 | Japan |
| 63-57549 | 3/1988 | Japan |
| 2181349 | 4/1987 | United Kingdom |
| 8809655 | 12/1988 | WIPO |

OTHER PUBLICATIONS

Antimicrobial Agents and Chemotherapy, vol. 31, No. 1, Jan. 1987, pp. 27–31; H. Thormar et al.

Journal of Dairy Science, vol. 59, No. 7, Jul. 1976, pp. 1203–1214, R. G. Jensen et al.

Archives of Virology, vol. 66, 1980, pp. 301–307, Springer-Verlag; A. Kohn et al.: "Unsaturated free fatty acids inactivate animal enveloped viruses".

Microbios Letters, vol. 35, 1987, pp. 71–78, The Faculty Press, Cambridge, GB; V. A. Merchant et al.: "Unsaturated free fatty acid inhibition of herpes simplex virus".

Antimicrobial Agents and Chemotherapy, vol. 15, No. 1, Jan. 1979, pp. 67–73; J. Sands et al.: "Extreme sensitivity of enveloped viruses, including herpes simplex, to long-chain unsaturated monoglycerides and alcohols".

Antimicrobial Agents and Chemotherapy, vol. 18, No. 6, Dec. 1980, pp. 962–968; A. Kohn et al.: "Interaction of polyunsaturated fatty acids with animal cells and enveloped viruses".

(List continued on next page.)

Primary Examiner—Zohreh Fay
Attorney, Agent, or Firm—Kane, Dalsimer, Sullivan, Kurucz, Levy, Eisele and Richard

[57] ABSTRACT

This invention is directed to antibacterial activity of fatty acids and monoglycerides. More particularly, this invention is directed to the killing of bacteria by fatty acids and monoglycerides. The invention is also directed to antibacterial pharmaceutical compositions consisting essentially of inert pharmaceutical carrier and an antibacterial effective amount of one or more compounds selected from the group consisting of fatty acids and monoglycerides thereof, fatty alcohols, and ethers and lysophosphatidylcholine derivatives.

17 Claims, No Drawings

OTHER PUBLICATIONS

Food Chem., vol. 4, No. 4, 1979, pp. 251–258, Applied Science Publishers Ltd. GB; G. Poli et al.: "Virucidal activity of organic acids".

Saheb et al., Chemical Abstracts, 90:67131v (1974).

Tsutsumi et al., Chemical Abstracts, 98:86086r (1983).

A. S. Cunningham, Morbidity in Breast–fed and Artificially Fed Infants, Journal of Pediatrics, 1979, vol. 95, No. 5, pp. 685–689.

M. G. Meyers et al., Respiratory and Gastrointestinal Illnesses in Breast– and Formula–fed Infants, Am. J. Dis. Child, 1984, vol. 138, pp. 629–632.

S. A. Larsen, Jr. et al., Relation of Breast versus Bottle Feeding to Hospitalization for Gastroenteritis in a Middle–class U.S. Population, Journal of Pediatrics, 1978 vol. 92, pp. 417–418.

M. E. Fallot et al., Breast–feeding Reduces Incidence of Hospital Admissions for Infection in Infants, Pediatr., 1980, vol. 65, No. 6, pp. 1121–1124.

A. S. Cunningham, Breast–feeding and Health, J. Pediatr., 1987, vol. 110, No. 4, pp. 658–659.

G. A. Loslonsky et al., Maternal–Neonatal Interactions and Human Breast Milk in Reproductive Immunology, N. Gleicher (ed.), New York, Allan R. Riss, 1981, pp. 171–182.

A. S. Goldman et al., Host Defenses: Development and Maternal Contributions, In: Advances in Pediatrics, L. A. Barnes (ed.), vol. 32, 1985, pp. 71–100.

J. K. Welsh et al., Use of Semliki Forest virus to Identify Lipid–Mediated Antiviral Activity and Anti–Alphavirus Immunoglobulin A in Human Milk, Infect. Immun., 1978, vol. 19, No. 2, pp. 395–401.

J. K. Welsh et al., Effect of Antiviral Lipids, Heat and Freezing on the Activity of Viruses in Human Milk, J. Infect. Dis., 1979, vol. 140, No. 3, pp. 322–328.

C. E. Isaacs et al., Membrane–Disruptvie Effect of Human Milk: Inactivation of Enveloped viruses, J. Infect. Dis., 1986, vol. 154, No. 6, pp. 966–971.

W. A. Falkler et al., A Lipid Inhibitor of Dengue Virus in Human Colostrum and Milk, Arch. Virol. 1975, vol. 47, pp. 3–10.

A. H. Fieldsteel, Nonspecific Antiviral Substances in Human Milk Active against Arbovirus and Murine Leukemia Virus Cancer Res., 1974, vol. 34, pp. 712–715.

T. H. Matthews et al., Antiviral Activity in Milk of Possible Clinical Importance, Lancet, 1976, vol. ii, pp. 1387–1389.

Sarker et al., Effect of Human Milk on the Mouse Mammary Tumor Virus, Cancer Res., 1973, vol. 33, pp. 626–629.

ANTIBACTERIAL FATTY ACID COMPOSITIONS

CROSS-REFERENCE TO RELATED APPLICATIONS

This is a combination of application(s) Ser. No. 07/896,120 filed Jun. 10, 1992, now abandoned, which is a continuation-in-part of co-pending U.S. patent applicaiton Ser. No. 543,111, filed Jun. 25, 1990 now pending, which is a continuation-in-part of co-pending U.S. patent application Ser. No. 365,291, filed Jun. 12, 1989 now pending, which is a continuation-in-part of U.S. patent application Ser. No. 140,078, filed Dec. 31, 1987, now U.S. Pat. No. 4,997,851.

FIELD OF THE INVENTION

This application is directed to spermicidal and antimicrobial activity of fatty acids and monoglycerides. More particularly, this application is directed to the spermicidal activity, inactivation of enveloped viruses and bacteria, and killing of cells by fatty acids and monoglycerides.

BACKGROUND OF THE INVENTION

There are many published reports concerning the ability of human milk to protect the suckling infant from gastrointestinal infection. See, A. S. Cunningham, Morbidity in breast-fed and artificially fed infants, *J. Pediatr.*, 1979, Vol. 95, p. 685–689; M. G. Myers et al., Respiratory and gastrointestinal illnesses in breast- and formula-fed infants, *Am. J. Dis. Child.*, 1984, Vol. 138, p. 629–632; S. A. Larsen, Jr., Relation of breast versus bottle feeding to hospitalization for gastroenteritis in a middle-class U.S. population, *J. Pediatr.*, 1978, Vol. 92, p. 417–418; M. E. Fallot et al., Breast-feeding reduced incidence of hospital admissions for infection in infants, *Pediatr.*, 1980, Vol. 65, p. 1121–1124; A. S. Cunningham, Breast-feeding and health, *J. Pediatr.*, 1987, Vol. 110, p. 658–659. Much of this protection has been attributed to the presence of immunogobulins in the milk. See, G. A. Loslonsky et al., Maternal-neonatal interactions and human breast milk, *In: Reproductive Immunology*, N. Gleicher (ed.), New York, Alan R. Riss, 1981, p. 171–182; A. S. Goldman et al., Host defenses: development and maternal contributions, *In: Barness LA.*, ed., *Advance in pediatrics*, Vol. 32, 1985, p. 71–100. However, it has also been shown that there are nonspecific factors in milk which can kill pathogens or slow their replication. Some of these protective factors are also nutrients, such as monoglycerides and fatty acids. Since human infant formula does not contain immunoglobulins, it has been assumed that it does not confer any protection against gastrointestinal infection. However, formulas do contain triglycerides which, following lipolysis in the stomach and intestine, produce free fatty acids and monoglycerides of which some have been shown to inactivate enveloped viruses and *Giardia lamblia* when present in human and bovine milk. See, J. K. Welsh et al., Use of Semliki Forest virus to identify lipid-mediated antiviral activity and anti-alphavirus immunoglobulin A in human milk, *Infect. Immun.*, 1978, Vol. 19, p. 395–401 (I); J. K. Welsh et al., Effect of antiviral lipids, heat, and freezing on the activity of viruses in human milk, *J. Infect. Dis.*, 1979, Vol. 140, p. 322–328 (II); C. E. Isaacs et al., Membrane disruptive effect of human milk: Inactivation of enveloped viruses, *J. Infect. Dis.*, 1986, Vol. 154, p. 966–971, all of the aforementioned articles being incorporated herein by reference.

Human milk contains a number of antiviral factors that are not immunoglobulins. See, W. A. Falkler, Jr., et al., A lipid inhibitor of dengue virus in human colostrum and milk, *Arch. Virol.*, 1975, Vol. 47, p. 3–10; A. H. Fieldsteel, Non-specific antiviral substances in human milk active against arbovirus and murine leukemia virus, *Cancer Res.*, 1974, Vol. 34, p. 712–715; T. H. Matthews et al., Antiviral activity in milk of possible clinical importance, Lancet, 1976, vol. ii, p. 1387–1389; N. H. Sarkar et al., Effect of human milk on the mouse mammary tumor virus, *Cancer Res.*, 1973, Vol. 33, p. 626–629. Some of these factors are located in the non-lipid fraction of the milk, but most studies found antiviral activity associated with the lipid fraction. Antiviral lipids were best characterized by Welsh et al. (II), who found that free unsaturated fatty acids and monoglycerides in milk inactivated enveloped, but not nonenveloped, viruses.

As reported in C. E. Isaacs et al., Membrane Disruptive Effect of Human Milk: Inactivation of Enveloped Viruses, *J. Infect. Dis.*, 1986, Vol. 154, p. 966–971, specifically incorporated herein by reference, the work of Welsh et al. (II) has been confirmed and extended. It was shown that lipids from fresh breast milk are not antiviral but become active against enveloped viruses upon storage at 4° C. and in infant stomachs, probably by the release of fatty acids from milk triglycerides.

OBJECTS OF THE INVENTION

It is an object of the invention to provide fatty acids and monoglycerides having spermicidal, antimicrobial, and cytocidal activity.

It is also an object of the invention to provide a method of killing sperm, inactivating microorganisms, or killing cells by contact with fatty acids and monoglycerides.

It is a further object of the invention to provide pharmaceutical compositions for killing sperm, microorganisms, or cells consisting essentially of inert pharmaceutical carrier and a spermicidal, an antiviral, or a cytocidal component consisting of a spermicidal, antiviral, or cytocidal effective amount of one or more compounds selected from the group consisting of $C_4$ to $C_{14}$ fatty acids and monoglycerides thereof and $C_{14}$ to $C_{22}$ mono- or polyunsaturated fatty acids and monoglycerides thereof.

These and other objects of the invention will become more apparent from the discussion below.

DISCUSSION

Many viruses that are virulent human pathogens have envelopes (pieces of membranes surrounding them). These include the AIDS virus (human immunodeficiency virus, HIV), and herpes viruses, including herpes simplex virus (HSV), Epstein-Barr virus (EBV), cytomegalovirus (CMV), Varicella/Zoster (VZ), Marek's disease virus, equine abortion virus, and pseudorabies virus. The viral envelope is essential for infectivity. While many compounds are able to destroy the envelope and inactivate the virus, a large number have toxic side effects in the body. Fatty acids and monoglycerides are normal metabolites in the body, notably formed during the breakdown of milk products. It has been found that fatty acids and/or monoglycerides may be successfully used for antiviral and/or antibacterial activities.

Lipids in fresh milk do not inactivate viruses but become antiviral after storage of the milk for a few days at 4° or 23° C. The appearance of antiviral activity depends upon active milk lipases and correlates with the release of free fatty acids in the milk. A number of fatty acids which are normal components of milk lipids were tested against enveloped viruses, i.e., vesicular stomatitis virus, herpes simplex virus, and visna virus, and against a nonenveloped virus, poliovirus. Short-chain and long-chain saturated fatty acids had no or a very small antiviral effect at the highest concentrations tested. Medium-chain saturated and long-chain unsaturated fatty acids, on the other hand, were all highly active against the enveloped viruses, although the fatty acid concentration required for maximum viral inactivation varied by as much as 20-fold. Monoglycerides of these fatty acids were also highly antiviral, in some instances at a concentration 10 times lower than that of the free fatty acids. None of the fatty acids inactivated poliovirus. Antiviral fatty acids were found to affect the viral envelope, causing leakage and at higher concentrations, a complete disintegration of the envelope and the viral particles. They also caused disintegration of the plasma membranes of tissue culture cells resulting in cell lysis and death. The same phenomenon occurred in cell cultures incubated with stored antiviral human milk. The antimicrobial effect of human milk lipids in vitro is therefore most likely caused by disintegration of cellular and viral membranes by fatty acids.

1. MATERIALS AND METHODS

Cell cultures. Vero cells (African green monkey kidney cell line; Flow Laboratories Inc., McLean, Va.) were grown in Eagle basal medium (BME) (GIBCO Laboratories, Grand Island, N.Y.) with 10% inactivated fetal bovine serum (GIBCO). Sheep fibroblast cultures were obtained from the choroid plexus of a lamb brain and grown in 15% lamb serum (Colorado Serum Co.) in BME. The maintenance medium (MM) for Vero cells was BME with 2% fetal bovine serum; for sheep cells, the MM was 2% lamb serum in BME. Gentamicin (0.1%) was added to all media.

Viruses. Vesicular stomatitis virus (VSV) strain Indiana and herpes simplex virus type 1 (HSV-1) strain MacIntyre were obtained from the American Type Culture Collection, Rockville, Md., and grown in Vero cells. Visna virus strain K796 was grown in sheep choroid plexus cells. Poliovirus type 1 strain Chat was obtained from R.I. Carp (New York Institute of Basic Research) and grown in Vero cells.

Virus titration. Viruses were titrated by inoculation of 10-fold dilutions (VSV, poliovirus, and HSV-1 were inoculated into Vero cell cultures, and visna virus was inoculated into sheep choroid plexus cell cultures) in 96-well microtiter tissue culture plates (Becton Dickinson Labware, Oxnard, Calif.). A virus dilution (0.1 ml) in MM was inoculated into each well with four wells per dilution. The plates were kept for 2 to 12 days, depending on the virus, and examined daily for cytopathic effect. Virus titers were calculated by the method of Reed and Muench (L. J. Reed et al., *Am. J. Hyg.*, 1938, Vol. 27, p. 493–497).

Milk samples. Human milk samples 1, 2, and 3 were collected under sterile conditions 1 to 5 months postpartum and kept deepfrozen at −86° C. until used in experiments.

Reagents. Fatty acids and monoglycerides were purchased from Sigma Chemical Co., St. Louis, Mo. (purest grade). Monoglyceride ethers were custom synthesized by Deva Biotech, Inc., Paoli, Pa. Immediately before use they were melted and emulsified in liquid form in BME with 10% fetal bovine serum by vortexing at the highest speed for 1 min. The emulsions (100 mg/ml) were diluted to the desired concentrations in MM. Emulsions of short-chain fatty acids were neutralized to pH 7 by addition of 1M NaOH. Unsaturated fatty acids and monoglycerides were kept under nitrogen, and emulsions were used within a few minutes of preparation. Eserine sulfate (physostigmine; Sigma) and NaCl were dissolved in water and diluted in MM before use in experiments.

Assay of antiviral activity. About $10^5$ 50% tissue culture infective doses ($TCID_{50}$) of virus were mixed with a five-fold dilution of milk in MM or with an emulsion of fatty acids and monoglycerides in MM and incubated at 37° C. for 30 min. Virus mixed with MM alone was used as a control. After incubation, the infectivity of each mixture was titrated by the serial dilution end-point method. Dilutions (10-fold) were made in MM. The $10^{-2}$ to $10^{-5}$ dilutions were inoculated into monolayers of Vero cells, and the virus titers were determined as described above. The difference between the titer ($\log_{10}$) of the control virus and the titers of milk-virus and lipid-virus mixtures, i.e., the reduction of virus titer, was used as a measure of antiviral activity.

Preparation of virus for electron microscopy. VSV was concentrated and partially purified by differential centrifugation in a Beckman L2-65B ultracentrifuge, and samples ($10^{10}$ $TCID_{50}$/ml) were incubated at 37° C. for 30 min. in Mm with or without emulsified fatty acids. The virus suspensions were applied to carbon-coated grids and negatively stained with 2% phosphotungstic acid, pH 7.0. Specimens were examined by using a Hitachi HS 8-2 electron microscope at 50 kV.

Preparation of cells for electron microscopy. Monolayer cultures of cells were incubated for 30 min. at 37° C. either in MM alone or with milk or a fatty acid emulsion. The cell layers were then carefully rinsed with Hanks balanced salt solution and fixed with 2% glutaraldehyde in 0.1M cacodylate buffer. After rinsing in buffer and postfixation with 2% osmium tetroxice, the cells were dehydrated through gradings of ethanol, critical-point dried, and sputter coated with 10.5 nm of gold. They were examined in an ISI-ISS40 scanning electron microscope at 20 kV.

Estimation of free fatty acids levels. Lipids from 100 μl of the milk samples were extracted with 0.5 ml of chloroform-methanol (2:1). The upper phase was removed, and an aliquot of the chloroform layer was separated by thin-layer chromatography on Silica Gel G (Merck & Co., Inc., Rahway, N.J.) plates with quantitative standards of oleic acid in a solvent system consisting of hexane-diethylether-acetic acid (70:30:1.5). The developed plates were charred after spraying with dichromatesulfuric acid, and the free fatty acids were quantitated by densitometry.

2. RESULTS

Relationship between lipolysis and antiviral activity. Previous results (Isaacs et al.) showed that human milk becomes active against enveloped viruses after storage at 4°, 23°, or −20° C. for various lengths of time. The antiviral activity is associated with the cream fraction, but the skim fraction is needed for the lipids to become antiviral. To test whether the appearance of antiviral activity depended on active milk lipases, milk samples 1, 2, and 3 were stored at 4° C. for 4 days with or without two lipase inhibitors, 5 mM eserine sulfate and 1M NaCl. The virus titer (VSV) fell from $10^5$ to $\leq 10^{1.5}$ TCID$_{50}$ after incubation with milk stored without an inhibitor, thus showing a reduction of $10^{3.5}$ TCID$_{50}$. In contrast, virus incubated in the same way with milk which had been stored with lipase inhibitors showed no loss of infectivity at the concentrations used. The inhibitors had no effect on milk which was already antiviral.

Another indication that the appearance of antiviral activity in stored human milk is associated with lipolysis is shown in the following table:

TABLE 1

Free fatty acids (FFA) and antiviral activity in milk

| Milk sample | Storage temp/time (°C./days) | FFA (mg/ml) | Reduction of VSV titer ($log_{10}$) | Lipoprotein lipase (U/ml) |
|---|---|---|---|---|
| 1 | −86/4 | 0.5 | 0 | 336 |
| | 23/4 | 12.0 | 4.0 | |
| | 4/4 | 7.0 | 4.0 | |
| 3 | −86/4 | 0.5 | 0 | 20 |
| | 23/4 | 2.0 | 0 | |
| | 4/4 | 2.0 | 0 | |

[a]The same results were obtained for milk tested fresh or after storage at −86° C.

According to Table 1, deep-frozen human milk sample 1 did not have a detectable level of free fatty acids, but the level increased to 7 and 12 mg/ml upon storage at 4° and 23° C., respectively, for 4 days. Both stored samples were highly antiviral. The free fatty acid level of milk sample 3, on the other hand, increased to only 2 mg/ml upon storage, and the milk did not become antiviral. Compared with milk sample 3, milk sample 1 had much higher levels of lipoprotein lipase, which was previously shown to correlate with the appearance of milk antiviral activity.

Antiviral activity of fatty acids and monoglycerides. A comparison of the antiviral activity of a number of fatty acids found in milk is shown in the following table:

TABLE 2

Viral inactivation by incubation with fatty acids at 37° for 30 min.

| Fatty Acid | Concn[a] in mg/ml (mM) | Reduction of virus titer ($log_{10}$) VSV | HSV-1 | VV[b] |
|---|---|---|---|---|
| Butyric (4:0)[c] | 10 (113) | 0 | ND[d] | ND |
| Caproic (6:0) | 10 (86) | 0 | ND | ND |
| Caprylic (8:0) | 10 (69) | 1.8 | ND | ≧3.2 |
| Capric (10:0) | 4 (22) | ≧4.0[e] | ≧4.0 | ≧3.2 |
| Lauric (12:0) | 2 (10) | ≧4.0 | ≧4.0 | ≧3.2 |
| Myristic (14:0) | 4 (16) | ≧4.0 | ≧4.0 | 1.7 |
| Palmitic (16:0) | 20 (78) | 1.0 | 1.0 | 0.7 |
| Palmitoleic (16:1) | 2 (15) | ≧4.0 | ≧4.0 | ≧3.2 |
| Stearic (18:0) | 20 (70) | 0 | ND | ND |
| Oleic (18:1 cis) | 2 (7) | ≧4.0 | ≧4.0 | ≧3.2 |
| Elaidic (18:1 trans) | 2 (7) | ≧4.0 | ND | ND |
| Linoleic (18:2) | 1 (3.5) | ≧4.0 | ≧4.0 | ≧3.2 |
| Linolenic (18:3) | 1 (3.6) | ≧4.0 | ≧4.0 | ≧3.2 |
| Arachidonic (20:4) | 0.5 (1.6) | ≧4.0 | ND | ND |

[a]Concentration of fatty acid in virus mixtures incubated at 37° C. for 30 min. All fatty acids were tested in a series of twofold concentrations. Shown is either the lowest concentration which reduced the VSV titer by ≧4.0 $log_{10}$ units of the highest concentration tested (butyric, caproic, caprylic, palmitic, and stearic).
[b]VV, Visna virus.
[c]Carbon atoms:double bonds.
[d]ND, Not done.
[e]The titer ($log_{10}$) of the control virus incubated with mm was 5.5, whereas no virus was detectable in the $10^{-2}$ to $10^{-5}$ dilutions of fatty acid-virus mixtures. It was not possible to test these mixtures in lower dilutions ($10^{-1}$ or undiluted) because they were toxic to the cell cultures. Assuming that the $10^{-1}$ dilution contained infectious virus, the highest possible titer of the fatty acid-virus mixture was $10^{1.5}$ $TCID_{50}$, and the reduction of virus titer ($log_{10}$) would equal 4.0 (5.5 minus 1.5). If the titers of the mixtures were less than $10^{1.5}$, the reduction of titer would be greater than 4.0.

It can be seen from Table 2 that short-chain (butyric, caproic, and caprylic) and long-chain saturated (palmitic and stearic) fatty acids had no or a very small antiviral effect at the highest concentrations tested. On the other hand, the medium-chain saturated and long-chain unsaturated fatty acids were all antiviral but at different concentrations. Table 2 shows the lowest concentration causing a 10,000-fold reduction in VSV titer. A 2-fold-lower concentration either did not inactivate the virus or caused only a 10-fold reduction in titer. Similar results were obtained for HSV-1 and visna virus, a retrovirus. In contrast, incubation of poliovirus at 37° C. for 30 min. with capric, lauric, myristic, palmitoleic, oleic, linoleic, linolenic, and arachidonic acids, each at a concentration of 8 mg/ml, did not cause a significant reduction of virus titer compared with the titer of poliovirus incubated without fatty acids ($10^{4.7}$ $TCID_{50}$). The sodium salts of oleic and linoleic acids had antiviral effects similar to those of the free acids.

Other products of lipolysis, e.g., 1-monoglycerides of fatty acids, were also tested for antiviral activity, as shown in the following table:

TABLE 3

Viral inactivation in human serum by incubation with monoglycerides at 37° C. for 30 min

| Monoglyceride | Concn[a] in mg/ml (mM) | Reduction of virus titer ($log_{10}$) VSV | HSV-1 |
|---|---|---|---|
| Monocaprylin (8:0)[b] | 2.0 (9) | ≧4.0 | ND[c] |
| Monocaprin (10:0) | 0.5 (2) | ≧4.0 | ≧3.7 |
| Monolaurin (12:0) | 0.25 (0.9) | ≧4.0 | ≧3.7 |
| Monomyristin (14:0) | 2.0 (13) | 3.0 | ND |
| Monoolein (18:1) | 1.0 (2.8[d]) | 2.3 | ND |
| Monolinolein (18:2) | 0.25 (0.7) | ≧4.0 | ND |

[a]Lowest concentration causing ≧3.0 $log_{10}$ reduction in virus titer.
[b]Carbon atoms:double bonds.
[c]ND, Not done.
[d]Highest antiviral activity of the concentrations tested (0.5 to 4 mg/ml). The same results were obtained when the monoglyceride was dissolved in ethanol and diluted 1:100 in mm before being added to the virus.

All the monoglycerides tested except monomyristin and monoolein were antiviral in concentrations 5 to 10 times lower (millimolar) than those of the corresponding fatty acids.

The above experiments with human milk, milk stomach contents, and purified lipids show that MGs and fatty acids which are released from human milk triglycerides either during storage or in the gastrointestinal tract kill enveloped viruses and very likely serve an in vivo protective role in breast-fed infants.

Studies have also been done to determine the time required for viral inactivation. Virus was incubated with monolaurin (12:0) in maintenance media:

TABLE 3A

Time Course of Viral Inactivation

| Incubation Time (min) | Reduction of HSV-L titer |
|---|---|
| 30 | ≧4.0 |
| 10 | ≧4.0 |
| 5 | ≧4.0 |
| 1 | ≧4.0 |
| 0.5 | ≧4.0 |

These results indicate that viral killing is rapid and probably happens as the MG or FFA comes into contact with the viral envelope. Electron micrographs with negative staining of VSV incubated with linoleic acid showed that at 0.5 mg per ml leakage of viral envelopes was produced allowing the stain to enter many particles. The effect was far more pronounced with 1 mg of linoleic acid per ml, causing particle disintegration.

Effect of fatty acids on viral particles. To study the effect of fatty acids on virus particles, VSV was concentrated, partly purified, and then incubated at 37° C. for 30 min in MM with or without linoleic acid. Negative staining of virus incubated without fatty acids showed an abundance of characteristic bullet-shaped particles covered with spikes and containing coiled nucleocapsids (see FIG. 1a of U.S. Pat. No. 4,997,851, incorporated herein by reference). Incubation with 0.5 mg of linoleic acid per ml caused leakage of viral envelopes, allowing the stain to enter many particles (see FIG. 1b of U.S. Pat. No. 4,997,851, incorporated herein by reference). The effect was far more pronounced with 1 mg of linoleic acid per ml (see FIG. 1c of U.S. Pat. No. 4,997,851, incorporated herein by reference), causing particle disintegration. Titration of the samples used for electron microscopy showed a 10-fold reduction in virus titer with 0.5 mg of linoleic acid per ml, whereas 1 mg/ml caused a ≧1,000-fold reduction. Similar results were obtained by negative staining of VSV incubated with low concentrations of arachidonic acid.

Disintegration of cell membranes by fatty acid. Negative staining of VSV treated with fatty acids suggested that virus inactivation results from disruption of the viral envelope, which is derived from the host cell plasma membrane. To study the effect on cell membranes, monolayers of Vero cells or sheep fibroblasts were incubated at 37° C. for 30 min. in MM with or without 1 mg of linoleic acid per ml and examined by scanning electron microscopy. Control cells incubated in MM without fatty acids showed intact cell membranes (see FIG. 2c of U.S. Pat. No. 4,997,851, incorporated herein by reference), whereas in cell layers treated with 1 mg of linoleic acid per ml, the cell membranes were partly or completely disintegrated (see FIG. 2d of U.S. Pat. No. 4,997,851, incorporated herein by reference), causing cell lysis. The same effect was seen by incubation of cells with human milk which had been stored at 4° C. for 4 days (see FIG. 2b of U.S. Pat. No. 4,997,851, incorporated herein by reference). This milk sample (no. 1) (Table 1) contained 7 mg of fatty acids per ml and was highly antiviral. On the other hand, milk sample 1 stored at −86° C. for 4 days (Table 1) showed no effect on cell membranes (see FIG. 2a of U.S. Pat. No. 4,997,851, incorporated herein by reference).

The micrographs in FIGS. 1a to 1c reflect negative staining of VSV particles showing the effect of linoleic acid treatment. Titration of the samples used for electron microscopy showed a ≦10-fold reduction in virus titer with 0.5 mg of linoleic acid per ml whereas 1 mg/ml caused a ≧10,000-fold reduction. Similar results were obtained by negative staining of VSV incubated with low concentrations of arachidonic acid.

It was next examined whether the effects of antiviral fatty acids were additive so that changes in the concentration of one antiviral component in a mixture can be compensated for by increasing or adding another fatty acid. Mixtures of fatty acids were made in which individual fatty acid concentrations had been found to either not inactivate the virus, or to reduce the titer by less than 10-fold. Mixtures were incubated with virus in maintenance medium. The results are set forth in the following table:

TABLE 4

Antiviral Activity of Fatty Acid Mixtures

| Fatty Acid Mixture | Individual Fatty Acid Conc. (mg/ml) | Total Fatty Acid Conc. (mg/ml) | Reduction of VSV titer (log$_{10}$) |
|---|---|---|---|
| Capric | 2 | 3 | ≧3.7 |
| Lauric | 1 | | |
| Lauric | 1 | 2 | ≧3.7 |
| Myristic | 1 | | |
| Lauric | 1 | 2 | ≧3.7 |
| Oleic | 1 | | |
| Oleic | 1 | .5 | ≧3.7 |
| Linoleic | 0.5 | | |
| Lauric | 0.7 | | |
| Oleic | 0.7 | 1.7 | ≧3.7 |
| Linoleic | 0.3 | | |

The ability to make antiviral mixtures of medium and long-chain fatty acids indicates that a balance can be made between the potentially toxic effects of high concentrations of medium chain fatty acids in vivo and the loss of antiviral long-chain fatty acids by binding to serum albumin and other blood proteins.

Effect of Antiviral Milk Samples on HIV Titers. Human milk and stomach contents samples that have been found to kill HSV-1 and VSV were tested against HIV (AIDS virus). The results are set forth in the following table:

TABLE 5

HIV Inactivation by Antiviral Human Milk

| Sample | Storage | Reduction of HIV titer (log$_{10}$) |
|---|---|---|
| 1 | Fresh | 0 |
| 1A | 4° C. | 5.0 |
| 2 | Fresh | 0 |
| 2A | 4° C. | 5.0 |
| 3 | Fresh | 0 |
| 3A | 4° C. | 3.5 |
| 4 | Fresh | 0 |
| 4A | Stomach Contents (3 hrs) | 3.0 |

As with assays of other enveloped viruses, HIV was diluted five-fold with sIgA depleted milk or stomach contents. Therefore, anti-HIV activity in the undiluted sample is greater than the 1,000 to 100,000-fold reduction in titer in the assay mix. The results also show that HIV is as sensitive to inactivation by milk lipids as the other enveloped viruses that were tested. It should, therefore, be possible to screen large numbers of lipid mixtures against HSV-1, for example, which is much less expensive to assay than HIV and then test only the promising mixtures against HIV.

Effect of an Antiviral Monoglyceride on CMV Titers. Monocaprin (10:0), which had previously been found to inactivate HSV-1 at a concentration of 2 mM, was tested against three separate CMV strains. Incubations were performed in a maintenance medium containing 10% serum. The results are set forth in the following table:

TABLE 6

Inactivation of CMV by a Purified Lipid

| CMV Strain Tested | Reduction of CNV Titer (log$_{10}$ TCID 50%)* |
|---|---|
| AD 169 | ≧3.69 |
| Espilat | ≧3.50 |
| Towne | ≧2.67 |

*TCID 50% - Tissue culture infective dose 50%, expressed as log$_{10}$.

The above results establish that CMV as well as HSV-1, HIV, and other enveloped viruses can be inactivated in a serum-containing medium.

Monoglyceride Inactivation of HSV-1 in Human Serum. HSV-1 was added directly to human serum, and virus inactivation was measured in the presence of either monocaprin (10:0) or monolaurin (12:0). The results are set forth in the following table:

TABLE 7

HSV-1 Inactivation in Human Serum

| Monoglyceride Added* | Conc. (mg/ml) | Reduction in HSV-1 titer ($log_{10}$) |
|---|---|---|
| Control | — | 0 |
| Monocaprin | 1 | 0.8 |
| Monocaprin | 2 | 1.8 |
| Monocaprin | 4 | ≧4.0 |
| Monolaurin | 1 | 0.8 |
| Monolaurin | 2 | 1.5 |
| Monolaurin | 4 | 2.0 |

*The incubation mixture contained human serum, HSV-1 (titer 5.5), and the indicated monoglyceride.

Monolaurin at 4 mg/ml reduced serum HSV-1 titer by only 100fold whereas monocaprin at the same concentration decreased the viral titer by ≧10 000-fold In our in vitro studies, monolaurin had more antiviral activity on a concentration basis (millimolar) than monocaprin. The serum results suggest that nonspecific interactions in serum and presumably plasma and other blood products are as important as inherent antiviral activity for determining which monoglycerides to add to human blood and blood products to inactivate viral pathogens.

Monoglyceride Inactivation of HSV-1 in Infant Formula. When monoglycerides were added to another complex fluid, infant formula (Enfamil), differences in HSV-1 killing were found as they were in human serum. The results are set forth in the following table:

TABLE 8

HSV-1 Killing in Infant Formula

| Monoglyceride Added* | Conc. (mg/ml) | Reduction in HSV-1 titer ($log_{10}$) |
|---|---|---|
| Monocaprin | 0.5 | 0 |
| Monocaprin | 1 | 0.3 |
| Monocaprin | 2 | 2.3 |
| Monolaurin | 0.5 | 0.3 |
| Monolaurin | 1 | 0.3 |
| Monolaurin | 2 | 1.0 |
| Monoolein | 0.5 | 0 |
| Monoolein | 1 | 0 |
| monoolein | 2 | 0 |
| Monolinolein | 0.5 | 0 |
| Monolinolein | 1 | 0.3 |
| Monolinolein | 2 | 0.5 |

*The incubation mixture contained formula, HSV-1, (titer 5.5), and the indicated monoglyceride.

As can be seen from the results set forth in Table 8, in infant formula, as in human serum, monocaprin appears to be the most effective monoglyceride against enveloped viruses. In maintenance medium monolinolein produced the same reduction in viral titer as monocaprin but at one-third the concentration (millimolar). Monocaprin at the concentration used was over 60-fold more effective in infant formula than monolinolein.

Effect of Added Monoglyceride on RBCs in Human Blood. A monocaprin concentration of 3 mg/ml that had previously been shown to be antiviral was added to whole human blood samples, and red blood cell counts were compared to those in the same sample before 1 ipid addition. The results are set forth in the following table:

TABLE 9

Stability of Red Blood Cells to Added Monoglyceride

| | Red Blood Cells* | |
|---|---|---|
| Sample | Untreated | Treated |
| 1 | 4.59 | 4.46 |
| 2 | 5.10 | 4.78 |
| 3 | 5.30 | 5.19 |
| 4 | 4.94 | 4.74 |
| 5 | 5.08 | 4.36 |

Units - $10^3/mm^3$

The results show that a monocaprin concentration that will kill ≧4.0 $log_{10}$ of enveloped virus when added to human serum does not lyse RBCs in whole blood.

Antibacterial Effect of Human Milk and Purified Monoglycerides. Fatty acids and monoglycerides are antibacterial as well as antiviral. Stomach contents (supplied by Dr. William C. Heird, Columbia Presbyterian Medical Center) from infant fed human milk by gastric intubation were tested for antibacterial activity against *Staphylococcus epidermidis* (gram +), *Escherichia coli* (gram −) and *Salmonella enteritidis* (gram −). See the following table:

TABLE 10

Antiviral and Antibacterial Activity of Human Milk Stomach Contents*

| | $Log_{10}$ Reduction in HSV-1 Titer by 1 Hour Human | $Log_{10}$ Reduction in Bacterial** Titer by 1 Hour Stomach Contents | | |
|---|---|---|---|---|
| Sample | Stomach Contents | S. edidermidis | E. coli | S. enteritidis |
| 1 | ≧4.0 | — | ≧5.0 | — |
| 2 | ≧4.0 | ≧5.0 | ≧4.0 | ≧4.0 |
| 3 | ≧4.0 | ≧4.0 | — | — |
| 4 | ≧4.0 | — | — | — |

*The milks themselves were all tested for antiviral and antibacterial activity, and none was detected.
**Each sample was not tested against all the bacterial strains because there was not a sufficient volume of stomach contents.

Stomach contents that were antiviral were also antibacterial, killing both gram+ and gram− bacteria. Since human milk contains both medium chain and long-chain fatty acids, it was next determined whether gram+ and gram− bacteria were equally sensitive to different chain lengths. The results are set forth in the following table:

TABLE 11

Inactivation of Gram+ and Gram− Bacteria by Monoglycerides
Reduction of bacterial concentration ($log_{10}$)

| Monoglyceride[1] | E.[2] coli | S.[2] enteritidis | H.[2,3] influenza | S.[4] epidermidis | Group B[4] streptococcus |
|---|---|---|---|---|---|
| Monocapryloyl (8:0) | ≧5.0 | — | ≧8.0 | ≧4.0 | — |
| Monocaprin (10:0) | ≧5.0 | — | ≧8.0 | ≧4.0 | 4.5 |
| Monolaurin (12:0) | 0 | 0 | ≧8.0 | ≧4.0 | 4.5 |
| Monoolein (18:1) | 0 | 0 | — | ≧4.0 | — |
| Monolinolein (18:2) | — | — | — | — | 4.5 |
| Monoeicosenoin | 0 | 0 | — | ≧4.0 | — |

TABLE 11-continued

Inactivation of Gram+ and Gram− Bacteria by Monoglycerides
Reduction of bacterial concentration ($\log_{10}$)

| Monoglyceride[1] | E.[2] coli | S.[2] enteritidis | H.[2,3] influenza | S.[4] epidermidis | Group B[4] streptococcus |
|---|---|---|---|---|---|
| (20:1) | | | | | |

[1] Each MG was used at 2 mg/ml.
[2] Gram−
[3] Hemophilus influenzas
[4] Grain+

Gram positive bacteria were inactivated comparably by medium chain saturated and long-chain unsaturated monoglycerides. However, the gram− bacteria *E. coli* and *S. enteritidis* were unaffected by long-chain unsaturated fatty acids and monolaurin. H. influenzae was inactivated by monolaurin so that there are differential sensitivities to MGs between different gram− bacteria. Differences in bacterial inactivation may be due to the bacterial wall, membrane or both. Scanning electron micrographs (not shown) of *S. epidermidis* treated with monolaurin showed that the bacteria were completely disintegrated. It is therefore possible to manipulate MGs and their concentrations to lyse some membranes and leave others intact.

Human milk becomes antiviral not only upon storage but also in the stomach of infants within one hour of feeding. The appearance of antiviral activity in stored milk is related to the level of lipoprotein lipase in the milk, indicating that it is caused by the release of fatty acids or other products of lipid hydrolysis. Similar results were previously reported by Welsh et al. (I, II). Data herein indicate that the antiviral effect of stored human milk is caused by lipolysis, and of the nine fatty acids most commonly found in human milk, seven are highly active in killing enveloped viruses. The polyunsaturated long-chain fatty acids were the most active, but medium-chain saturated fatty acids, particularly lauric and myristic acids, also showed activity. Monocaprin and monolaurin were active in concentrations ten times lower than those of the corresponding free acids, but monomyristin was consistently less active. Long-chain saturated fatty acids, which make up about 30% of the fatty acids in human milk, and short-chain fatty acids, which are more common in cow milk, were not, or were very slightly, antiviral. The concentrations of fatty acids found to reduce viral titers by $\geq$10,000-fold in vitro (Table 2) are in the same range of fatty acid concentrations found in human milk. The results indicate that as lipolysis of milk triglycerides proceeds, either during storage or in the gastrointestinal tract, two types of antiviral lipids, monoglycerides and free fatty acids, are produced. It is possible that these two classes of lipid differ in efficacy against intestinal pathogens. This may also be true for the members of each lipid class.

The results are similar to those of earlier studies with different viruses and further establish the marked antiviral effect of most fatty acids found in milk. The electron microscope study suggests that the antiviral effect is caused primarily by disintegration of viral envelopes by fatty acids. Similar findings were reported by Sarkar et al., who treated mouse mammary tumor virus with the cream fraction of human milk and noted degradation of the viral envelope. Our study also shows disintegration of the plasma membrane of cultured cells with concentrations of fatty acids and stored human milk that inactivate enveloped viruses. The fatty acids and monoglycerides which have been found to be strongly antiviral were shown to induce fusion of cell membranes. Although the exact mechanism is not clear, it has been suggested that the fatty acids and their monoesters are incorporated into the lipid membrane, causing destabilization of the bilayer. A similar mechanism might lead to the complete disintegration of cell membranes and viral envelopes we observed. The sensitivity of cultured cells and enveloped viruses at various fatty acid concentrations were not compared.

Several studies have indicated a lower incidence of infections, particularly gastrointestinal, in breast-fed versus bottle-fed infants. However, the role of milk fatty acids and their derivatives in protecting babies against illness is not established, despite their well-known antimicrobial effect in vitro. Although most known gastrointestinal viruses are nonenveloped, necrotizing enterocolitis in infants is caused by an enveloped virus, i.e., a human enteric coronavirus. Also, pestiviruses, which are enveloped, cause gastroenteritis in human infants and animals. Giardia lamblia, an intestinal protozoan parasite infecting children, is killed by milk fatty acids in vitro, suggesting the possibility of a giardiacidal effect of fatty acids in the intestines. Since fatty acids lyse cells by disrupting their plasma membranes, it is likely that they kill not only giardia but also other parasitic protozoa. Although a few studies have demonstrated antimicrobial activity of human and animal stomach contents after milk feeding, much more work is needed to characterize the active factors and to establish their role in prevention of, and recovery from, gastrointestinal infections.

It is within the scope of the invention that fatty acids and/or monoglycerides thereof are used for spermicidal, antimicrobial, especially antiviral and/or antibacterial, or cytocidal activity. The compounds used can be selected from the group consisting of saturated or unsaturated fatty acids having from 4 to 22 carbon atoms, esters or ethers of glycerol with said acids, and saturated or unsaturated fatty alcohols having from 4 to 22 carbon atoms, especially from 6 to 14 carbon atoms. Preferred compounds comprise saturated fatty acids having from 4 to 14 carbon atoms, particularly from 6 to 14 carbon atoms, and monoglycerides thereof, and saturated fatty alcohols having from 6 to 14 carbon atoms. Especially preferred are $C_7$–$C_{12}$ fatty acid monoglycerides, either singly or in mixtures thereof. Also useful according to the invention are mono- or polyunsaturated fatty acids having from 14 to 22 carbon atoms, especially from 16 to 20 or from 16 to 18 carbon atoms, and the monoglycerides thereof, and mono- or polyunsaturated fatty alcohols having from 14 to 22 or 16 to 20 carbon atoms. The above-mentioned ranges of carbon atoms are inclusive of fatty acids having odd numbered carbon atoms.

It is also within the scope of the invention to employ ether and/or lysophosphatidylcholine derivatives of $C_4$–$C_{22}$ fatty acids having antimicrobial, especially antiviral and/or anti-bacterial, activity. For example, useful fatty acid derivatives would have an ether bond between a fatty acid and glycerol. Examples of such compounds include 1-O-decyl-sn-glycerol, 1-O-lauryl-sn-glycerol, 1-O-octyl-sn-glycerol, and 1-O-oleyl-sn-glycerol. Useful lysophosphatidylcholine derivatives include, for example, L-α-lysophosphatidylcholine caproyl, L-α-lysophosphatidylcholine decanoyl, and L-e- lysophosphatidycholine lauroyl. Also, the fatty acids useful according to the invention can be used in the form of their pharmacologically acceptable salts, such as alkali metal salts. Useful examples of such salts include the sodium and lithium salts.

The compounds according to the invention can be used singly or in mixtures. For example, it is preferred that from 1 to 6 compounds, especially from 1 to 4 compounds, be administered at one time.

The results of testing reflecting the usefulness of monoglyceride ethers and lysophosphatidylcholine derivatives are shown in the following tables:

TABLE 12

Inactivation of vesicular stomatitis virus by monoglyceride ethers in human plasma[1]

| Monoglyceride Ether | Concentration (mM) | Sodium Taurocholate (10 mM) | Reduction in VSV Titer ($Log_{10}$) |
|---|---|---|---|
| 1-O-Decyl-sn-glycerol[3] | 5 | + | 0 |
| 1-O-Octyl-sn-glycerol[2] | 10 | — | ≧4.0 |
|  | 10 | — | 2.0 |
| 1-O-Octyl-sn-glycerol | 15 | — | ≧4.0 |
| 1-O-Octyl-sn-glycerol | 5 | + | ≧4.0 |
|  | 10 | — | 1.3 |
|  | 15 | — | ≧4.0 |
| 1-O-Oleyl-sn-glycerol[4] | 5 | — | 0 |
|  | 10 | — | 0 |
|  | 15 | — | 0 |

[1]Incubations were done at 37° for 30 minutes.
[2]8 carbon ether.
[3]10 carbon ether.
[4]18 carbon ether.

TABLE 13

The antiviral activity of monoglyceride esters and ethers is additive[1]

| Ether (Carbons) | Concn. (mM) | Ester (Carbons) | Concn. (mM) | Sodium Taurocholate | Concn. (mM) | Reduction in VSV Titer ($log_{10}$) |
|---|---|---|---|---|---|---|
| 8 | 5 | 8 | 5 | — | — | 0 |
| 8 | 7.5 | 8 | 7.5 | — | — | 3.7 |
| 8 | 5 | 8 | 5 | + | 5 | ≧4.0 |
| 8 | 2.5 | 8 | 2.5 | + | 10 | ≧4.0 |
| 10 | 5 | 10 | 5 | — | — | 2.0 |
| 10 | 7.5 | 10 | 7.5 | — | — | 1.8 |
| 10 | 5 | 10 | 5 | + | 5 | ≧4.0 |
| 10 | 2.5 | 10 | 2.5 | + | 10 | ≧4.0 |
| 8 | 2.5 | 8 | 2.5) | — | — | 1.3 |
| 10 | 2.5 | 10 | 2.5) |  |  |  |
| 8 | 2.5 | 8 | 2.5) | + | 5 | ≧4.0 |
| 10 | 2.5 | 10 | 2.5) |  |  |  |

[1]Incubated at 37° for 30 minutes in human plasma.

TABLE 14

Time course of VSV inactivation at 37° in human plasma with 15 mM 1-O-octyl-sn-glycerol

| Incubation Time (min.) | Reduction in VSV Titer ($Log_{10}$) |
|---|---|
| 2.5 | 0 |
| 5 | ≧4.0 |
| 10 | ≧4.0 |
| 15 | ≧4.0 |
| 30 | ≧4.0 |

The 8 carbon and 10 carbon MG ethers are just as effective as the naturally occurring esters, and, in fact, the 8 carbon derivative appears to be somewhat more antiviral than the 8 carbon ester. The 18 carbon ether (Table 12) showed the same lack of antiviral activity as the ester in human plasma.

TABLE 15

Antiviral Activity of Lysophosphatidylcholine Derivatives

| Lipid | Conc (mM) | Sodium Taurocholate (10 mM) | $Log_{10}$ Reduction in VSV Titer |
|---|---|---|---|
| L-α-Lysophosphatidylcholine caproyl (8 C.) | 5 | + | 0 |
|  | 5 | — | 0 |
|  | 10 | + | 0 |
|  | 10 | — | 0 |
|  | 15 | + | 1.0 |
|  | 15 | — | 0 |
| L-α-Lysophosphatidylcholine | 5 | + | 1.7 |
|  | 5 | — | 1.7 |
| decanoyl (10 C.) | 10 | + | 1.7 |
|  | 10 | — | 1.0 |
| L-α-Lysophosphatidylcholine lauroyl (12 C.) | 5 | + | 1.7 |
|  | 5 | — | 1.2 |
|  | 10 | + | 2.0 |
|  | 10 | — | 2.0 |

The activity of the aforesaid fatty acids and/or monoglycerides (esters) can be enhanced by the presence of an effective amount of blood enzyme lipase (LPL) inhibitors. LPL breaks down the preferred fatty acid monoglycerides into constituent free fatty acids and glycerol, which is significant because while the free fatty acids are also antiviral, they often require a much higher concentration than the corresponding monoglycerides to be effective in human blood. Also, fatty acids can pass through the blood brain barrier while the corresponding monoglycerides can not. LPL inhibitors reduce or deter such breakdown. Useful LPL inhibitors include, for example, the following:

1) Bile salts or acids and conjugated bile salts or acids, at concentrations of from about 1 nanomolar to 1 molar.

An example of a conjugated bile acid is taurocholic acid, the sodium and lithium salts of which are readily available. Bile salts are also detergents, and therefore they provide additional antimicrobial or antiviral activity;

2) Sodium chloride, at concentrations of from about 1 micromolar to 10 molar; and 3) Protamine chloride or sulfate, at concentrations of from about 1 nanomolar to 1 molar.

When LPL inhibitors are used with, for example, monoglycerides according to the invention, they can be used in an mM:mM ratio of from about 1:1 to 1:6, based upon the monoglyceride or monoglycerides used. Preferably this ratio is from about 1:1.5 to 1:4.

To demonstrate the effectiveness of, for example, the conjugated bile acid taurochloric acid (sodium salt), an incubation mixture containing herpes antibody negative human serum, herpes simplex virus-1 (titer) 5.5, and a monoglyceride, was prepared. A quantity of 12 mM (final concentration) sodium taurochlorate was added to some of the samples. The results were as follows:

TABLE 16

| Monoglyceride Added | Sodium Taurocholate | Reduction in Herpes Simplex Virus-1 Titer ($\log_{10}$) |
|---|---|---|
| 1-Monocapryloyl-rac-Glycerol (8:0) 7.5 mM | + | $\geq 4.0$ |
|  | − | 0 |
| 1-Monodecanoyl-rac-Glycerol (10:0) 7.5 mM | + | $\geq 4.0$ |
|  | − | 0 |
| 1-Monodecanoyl-rac-Glycerol (10:0) 15 mM | + | $\geq 4.0$ |
|  | − | 3.0 |

In analogous procedures additional testing of the effectiveness of sodium taurocholate in human serum was performed. The results are set forth in the following tables:

TABLE 17

| 1-Monocapryloyl-rac-glycerol (mM) | 1-Monodecanoyl-rac-glycerol (mM) | Sodium Taurocholate (mM) | Reduction in VSV Titer ($\log_{10}$) |
|---|---|---|---|
| 7.5 | — | 12 | $\geq 5.0$ |
| — | 7.5 | 12 | $\geq 5.0$ |
| 7.5 | — | 10 | $\geq 5.0$ |
| — | 7.5 | 10 | $\geq 5.0$ |
| 7.5 | — | 8 | $\geq 5.0$ |
| — | 7.5 | 8 | $\geq 5.0$ |
| 7.5 | — | 6 | $\geq 5.0$ |
| — | 7.5 | 6 | $\geq 5.0$ |
| 7.5 | — | 4 | 4.0 |
| — | 7.5 | 4 | $\geq 5.0$ |
| 7.5 | — | 2 | $\geq 3.0$ |
| — | 7.5 | 2 | $\geq 5.0$ |
| 7.5 | — | 0 | $\geq 1.0$ |
| — | 7.5 | 0 | 1.0 |

TABLE 18

| 1-Monolauroyl-rac-glycerol (mM) | Sodium Taurocholate (mM) | Reduction in VSV Titer ($\log_{10}$) |
|---|---|---|
| 15 | 10 | $\geq 5.0$ |
| 15 | — | 0 |
| 7.5 | 10 | $\geq 5.0$ |
| 7.5 | — | 0 |
| 5 | 10 | $\geq 5.0$ |
| 5 | — | 0 |
| 4 | 10 | $\geq 5.0$ |
| 4 | — | 0 |

TABLE 18-continued

| 1-Monolauroyl-rac-glycerol (mM) | Sodium Taurocholate (mM) | Reduction in VSV Titer ($\log_{10}$) |
|---|---|---|
| 3 | 10 | $\geq 5.0$ |
| 3 | — | 0 |

Table 17 shows that when 1-monocapryloyl-rac-glycerol and 1-monodecanoyl-rac-glycerol monoglycerides are used with varying concentrations of sodium taurocholate, the 1-monodecanoyl-rac-glycerol is effective when used with concentrations as low as 2 mM sodium taurocholate whereas the 1-monocapryloyl-rac-glycerol needs at least 6 mM sodium taurocholate to be effective. The 1-monocapryloyl-rac-glycerol monoglyceride is still more likely to be used in a product, however, because it is more soluble.

Table 18 shows that the 1-monolauroyl-rac-glycerol monoglyceride also kills vesicular stomatitis virus at concentrations as low as 3 mM in the presence of 10 mM sodium taurocholate. Also, Table 18 shows that viral killing by 1-monolauroyl-rac-glycerol monoglyceride only takes place when sodium taurocholate is present.

Further testing was conducted to demonstrate the effectiveness of sodium taurocholate in human plasma. The results were as follows:

TABLE 19

| 1-Monocapryloyl-rac-glycerol (mM) | 1-Monodecanoyl-rac-glycerol (mM) | Sodium Taurocholate (1 mM) | Reduction in VSV titer ($\log_{10}$) |
|---|---|---|---|
| 4 | — | 10 | 2.0 |
| 4 | — | — | 0 |
| 7.5 | — | 10 | $\geq 4.0$ |
| 7.5 | — | — | 1.0 |
| 15 | — | 10 | $\geq 4.0$ |
| 15 | — | — | 2.0 |
| — | 4 | 10 | 1.0 |
| — | 4 | — | 0 |
| — | 7.5 | 10 | $\geq 4.0$ |
| — | 7.5 | — | 1.0 |
| — | 15 | 10 | $\geq 4.0$ |
| — | 15 | — | $\geq 4.0$ |

The additional antiviral activity in the presence of sodium or lithium taurocholate is due not only to LPL inhibition but also to detergent activity of these compounds. In fact, the results presented below show that in phosphate buffer as little as 5mM sodium taurocholate can inactivate VSV. However, in human plasma a sodium taurocholate concentration of at least 20mM is required to kill $\geq 4.0$ $\log_{10}$ of VSV, and therefore taurocholate by itself may not be desirable for use in human blood and blood products used for transfusion.

TABLE 20

Inactivation of VSV by Sodium Taurocholate in Phosphate Buffer and Human Plasma

| Sodium Taurocholate (mM) | Reduction of VSV titer ($\log_{10}$) | |
|---|---|---|
|  | Phosphate Buffer | Plasma |
| 0 | 0 | 0 |
| 2.5 | 1.0 | 0 |
| 5 | $\geq 4.0$ | 0 |
| 10 | $\geq 4.0$ | 0 |
| 15 | $\geq 4.0$ | 1.0 |
| 20 | $\geq 4.0$ | 3.7 |

The importance of LPL inhibitors for the antiviral activity of monoglycerides depends upon the endogenous LPL activity in each blood sample. Since LPL activity is variable and each blood sample will not be tested for LPL activity, it would be preferred to add LPL inhibitors and monoglycerides to each clinical blood sample to ensure maximum antiviral activity. Also, since the addition of lithium taurocholate does not interfere with any clinical assays tested, it provide added antiviral activity with no drawbacks.

Fatty acids and monoglycerides thereof are readily available. Should it be necessary, desired monoglycerides can be prepared from the corresponding fatty acid or acids by esterification with glycerol according to known procedures.

The above-described compounds have demonstrated antimicrobial, especially antiviral and/or antibacterial, activity. It is within the scope of this invention that media containing microorganisms, such as virus or bacteria-containing media, e.g., blood, can be treated with an effective amount of one or more fatty acids and/or monoglycerides thereof. It is also within said scope that a human, warm-blooded animal, or plant having a microbial condition may be treated for said condition by administration of a composition according to the invention. As is set forth herein, the compounds of the invention have antimicrobial, especially antiviral and/or antibacterial, activity. Microorganisms that can be killed according to the invention include, but are not limited to, the following fungi, yeast, and viruses:

| | Fungi |
|---|---|
| Ringworm: | Dermatophytes |
| | Black piedra |
| | White piedra |
| | Tines nigra |
| | Tines versicolor |
| | Yeast |
| Yeast: | Candida albicans |
| | Viruses |
| Togaviridae family: | |
| Alphavirus (arbovirus group A) | mosquito-borne viruses |
| Flavivirus (arbovirus group B) | mosquito-borne viruses |
| | tick-borne viruses |
| Rubivirus | Rubella virus |
| Pestivirus | viruses of cattle and pigs |
| Orthomyxoviridae: | Influenza virus A |
| | Influenza virus B |
| | Influenza virus C |
| Paramyxoviridae: | Parainfluenza virus |
| | Mumps virus |
| | Newcastle disease virus |
| | Viruses of rinderpest and canine distemper virus |
| | respiratory synoytial virus |
| | rabies viruses |
| Retroviridae: | sarcoma and leukemia viruses |
| | visna virus |
| | human immuno deficiency viruses (AIDS) |
| | human lymphotropic viruses Types 1 and 2 |
| Herpesviridae: | Herpes simplex types 1 and 2 |
| | varicella zoster |
| | cytomegalovirus |
| | Epstein-Barr virus |
| | All other members of this group |

The fatty acids and derivatives thereof disclosed here are useful as spermicides and in the treatment of sexually transmitted diseases. To demonstrate the spermicidal aspects of the invention 1-O-octyl-sn-glycerol and N-dodecylsucrose were tested against semen. Four samples tested were comprised as follows:

| Sample | Compound | Concentration (mM)* |
|---|---|---|
| A | 1-O-octyl-sn-glycerol | 150 |
| B | 1-O-octyl-sn-glycerol | 100 |
| C | N-dodecylsucrose | 150 |
| D | N-dodecylsucrose | 100 |

*In semen

Five test tubes were prepared, one for each of Samples A to D and a Control. An amount of 0.5 ml of active semen was added to each test tube. Each of Samples A and B and the Control was at 37° C., and Samples C and D were at room temperature. The percentages of motility and viability were measured from 15 seconds to 5 minutes in the case of each of Samples A to D and from 15 seconds to 2 hours for the Control. The results were as follows:

TABLE 21

| | Sample A | | Sample B | | Sample C | | Sample D | | Control | |
|---|---|---|---|---|---|---|---|---|---|---|
| Time | % mot. | % via. | % mot. | % via. | % mot. | % via. | % mot. | % via. | % mot | % via. |
| 15 sec. | 0 | * | 0 | * | 0 | * | 17 | * | 63 | 64 |
| 30 sec. | 0 | * | 0 | * | 0 | * | 9 | * | 63 | 64 |
| 1 min. | 0 | * | 0 | * | 0 | * | 2 | * | 63 | 64 |
| 2 min. | 0 | * | 0 | * | 0 | * | 0 | * | 63 | 64 |
| 3 min. | 0 | 0 | 0 | 0 | 0 | 0 | 0 | * | 63 | 64 |
| 5 min. | 0 | 0 | 0 | 0 | 0 | 0 | 0 | 0 | 63 | 64 |
| 10 min. | — | — | — | — | — | — | — | — | 63 | 64 |
| 15 min. | — | — | — | — | — | — | — | — | 63 | 64 |
| 30 min. | — | — | — | — | — | — | — | — | 62 | 64 |
| 1 hr. | — | — | — | — | — | — | — | — | 62 | 64 |
| 2 hrs. | — | — | — | — | — | — | — | — | 60 | 63 |

*Unable to perform

It was noted that Solutions A, B, and C coated the sperm effectively whereby only small portions of the sperms' heads or tails were exposed for examination after 30 minutes, Solution C being most effective in this regard. Solution D did not have any coating effect at all. Solutions A, B, and C rendered the sperm cells immobile within 15 seconds of exposure and effected 0% viability within 3 minutes. No lysis of sperm cells was noted on any samples within 2 hours.

For treatment, prophylaxis, antimicrobial, cytocidal, and/or antibacterial purposes one or more of the compounds described herein can be administered to a human or warm-blooded animal perorally, parenterally, intravenously, topically, vaginally, or rectally as active ingredient in customary pharmaceutical compositions, that is, compositions consisting essentially of an inert pharmaceutical carrier and an effective amount of active ingredient, such as tablets, coated pills, capsules, wafers, powders, solutions, suspensions, emulsions, suppositories, creams, and the like. An effective amount for such application of the compounds according to the present invention would be on the order of from about 0.001 to 4 mg/kg of body weight, preferably from about 0.01 to 3 mg/kg of body weight, 1 to 4 times daily.

Notwithstanding the above, administration to humans, plants, or warm-blooded animals, such as pets, may vary greatly regarding the carrier and amount of active ingredient. For example, administration of an antimicrobial agent to a plant could consist of an aqueous solution containing from about 10 μg/ml to 1000 mg/ml of active ingredient, added to soil or a cream containing from about 25 μg/ml to 500 mg/ml of active ingredient. Subject to any existent administrative limitations, an effective, spermicidal, antimicrobial, cytocidal, or antibacterial amount of active ingredient is to be administered in an appropriate vehicle as would be appreciated by those skilled in the art.

The naturally occurring ester derivatives are antiviral and do not interfere with the clinical assays examined with the exception of triglyceride measurements. Since triglyceride concentration is determined by the enzymatic release of fatty acids from the glycerol backbone, monoglycerides push these measurements off scale on the high side. By using ether linkages rather than ester linkages, the fatty acid remains attached to the glycerol backbone because lipases do not work on ether linkages and the triglyceride measurements are unaffected.

While, as shown above, sodium taurocholate is effective as an LPL inhibitor and has antiviral activity, other physiologically acceptable salts, such as lithium salts, are notable. By use of lithium taurocholate instead of the sodium salt, any interference with blood sodium measurements has been eliminated. In some testing a combination of monoglyceride ether and lithium taurocholate was in excess of what is needed to inactivate ≧4 log$_{10}$ of any enveloped virus in all of the blood and blood products examined.

Further testing has shown the effect of monoglyceride esters and ether on the total white blood cell concentration in whole human blood. The results of said testing are as follows:

TABLE 22

Stability of white blood cells in whole human blood to added lipid

| Sample | Concentration (mM) | Total White Blood Cells |
| --- | --- | --- |
| Control | — | 6.4 |
| 1-Monocapryloyl-rac-glycerol | 15 | 2.4 |
| 1-O-Octyl-sn-glycerol | 15 | 0.6 |
| 1-monodecanoyl-rac-glycerol | 15 | 0.7 |
| 1-O-Decyl-sn-glycerol | 15 | 1.31 |

To further appreciate the invention, it should be noted that monoglycerides added to human blood and human serum have been found to inactivate viruses present yet have no adverse effect on the serum or the red blood cells. This is of particular interest in blood handling procedures and equipment.

8 to 10 carbon monoglyceride (MG) at a concentration of 4 mg/ml did not interfere with 17 commercially available Abott's diagnostic test kits and MA bioproduct test kits. The Abott's kits tested were: HBsAg (hepatitis B surface antigen); Anti-HBc (anti-hepatitis B core antigen); Anti-HBs (anti-hepatitis B surface antigen); Anti-HBcIgM (anti-hepatitis B core IgM); Anti-HAVIgM (hepatitis Be antigen); Anti-HBe (anti-hepatitis B antigen); Anti-delta hepatitis. The MA Bioproduct ELISA kits tested were: mumps antibody; Herpes simplex type I antibody; Herpes Simplex type II antibody; Toxoplasmosis antibody; CMV antibody; Rubella antibody; Measles antibody; and Chlamydia antibody. Positive and negative test results remained consistent among the control and mg treated samples. The test results are set forth in, for example, co-pending U.S. patent application Ser. No. 365,291, filed Jun. 12, 1989, and PCT Published Application No. PCT/US90/03300, both of which are incorporated herein by reference.

Addition of fatty acids did not interfere with routine blood tests. However, the addition of monoglyceride esters interferes with triglyceride measurements. The use of monoglyceride ethers eliminates this problem.

Also, additional testing has shown that the presence of LPL inhibitors, such as are described above, does not interfere with the results and/or effectiveness of the above-described test kits.

Certain applications of the antimicrobial compounds and compositions described herein can be more readily appreciated by reference to FIGS. 1 to 4 of co-pending U.S. patent application Ser. No. 365,291, filed Jun. 12, 1989, incorporated herein by reference. In said application, equipment for handling blood products such as blood sera is treated with effective amounts of antiviral or antibacterial active ingredients. For example, coated test tubes, vacutainer tubes, and other blood handling items are disclosed. Other potential applications disclosed for the spermicidal, antimicrobial, cytocidal, and antibacterial monoglycerides and fatty acids include: facial cream (as an acne treatment), bactericidal, fungicidal, virucidal; shampoo, hand lotion; athlete's foot medication (ointment, powder, soap); candies (for sore throat, bad breath, recurrent herpes); ointment or foam spray (for genital herpes legion treatment); shaving cream; mouth wash; after shave lotions; tooth paste; diaper rash preventer; plasma bag treatment; disposable glove treatment; additive to pasteurized cow milk; additive to blood sample tubes to inactivate HIV, HCMV, and other viruses (safety measure for lab technicians and healthcare providers); additives for condoms, band-aids, or bandages; additive for paint; or animal or plant treatment for microbial infections.

Where certain spermicidal, antimicrobial, cytocidal, or antibacterial usage is intended, a spermicidal, antimicrobial, cytocidal, or antibacterial effective amount of a fatty acid or derivative thereof is applied with a carrier to the outer surface or surfaces of an appropriate vehicle. For example, a condom or diagram could be coated wholly or partially with dry or liquid, preferably, viscous, coating material containing a spermicidally effective amount of fatty acids or derivatives thereof.

Also, while reference is made to spermicidal, antimicrobial, cytocidal, or antibacterial activity, it should be noted that activity against sexually transmitted diseases is intended. Such sexually transmitted diseases include, but are not limited to, herpes, chlamydia, syphilis, and gonorrhea, HIV, and other retroviruses, such as HTLV-I and HTLV-II.

Further, it should be understood that the antimicrobial or other activity of the invention is not limited to a specific medium. For example, the compounds disclosed herewith can inactivate enveloped viruses in virtually any medium, including, but not limited to, blood, blood products, plasma, plasma derivatives, growth or nutrient media, water, various body fluids and virtually any other medium that would be compatible with, i.e., not destructive to, the compounds disclosed herein. It is meant to specifically include any mixture, solution, or product useful in, or resulting from, any bio-engineering or genetic engineering procedure as well as the elimination of infectious agents from any biological products. The compounds disclosed herein could be added in an antiviral or antimicrobial effective amount to said medium or the medium could be contacted with said compounds or a substrate containing said compounds.

The preceding specific embodiments are illustrative of the practice of the invention. It is to be understood, however, that other expedients known to those skilled in the art or disclosed herein may be employed without departing from the spirit of the invention or the scope of the appended claims.

We claim:

1. A method of preventing or treating a bacterial condition in a host human or warm-blooded animal in need thereof, which comprises perorally, parenterally, intravenously, topically, vaginally, or rectally administering to said host an effective antibacterial amount of an antibacterial component comprising one or more compounds selected from the group consisting of $C_6$–$C_{14}$ fatty acid monoglycerides, and $C_7$–$C_{12}$ fatty alcohols.

2. The method of claim 1, wherein the antibacterial component also comprises an effective amount of LPL inhibitor.

3. The method of claim 2, wherein the LPL inhibitor is sodium or lithium taurocholate.

4. The method of claim 1, wherein the antibacterial component comprises from 1 to 4 compounds.

5. A method of preventing or treating a bacterial condition in a host human or warm-blooded animal in need thereof, which comprises perorally, parenterally, intravenously, topically, vaginally, or rectally administering to said host an effective antibacterial amount of an antibacterial component comprising one or more compounds selected from the group consisting of $C_{16}$–$C_{20}$ mono- or polyunsaturated fatty acids and monoglycerides thereof, and $C_{16}$–$C_{20}$ mono- or polyunsaturated fatty alcohols.

6. A method of preventing or treating a bacterial condition in a host human or warm-blooded animal in need thereof, which comprises perorally, parenterally, intravenously, topically, vaginally, or rectally administering to said host an effective antibacterial amount of an antibacterial component comprising one or more compounds selected from the group consisting of ether and lysophosphatidylcholine derivatives of $C_4$–$C_{22}$ fatty acids.

7. The method of claim 6, wherein the antibacterial component comprises one of more compounds selected from the group consisting of 1-O-decyl-sn-glycerol, 1-O-lauryl-sn-glycerol, 1-O-octyl-sn-glycerol, 1-O-oleyl-sn-glycerol, L-α-lysophosphatidylcholine caproyl, L-e-lysophosphatidylcholine decanoyl, and L-α-lysophosphatidylcholine lauroyl.

8. An antibacterial composition for preventing or treating a bacterial condition or a host human or warm-blooded animal by topical, peroral, parenteral, intravenous, vaginal, or rectal administration, which comprises an effective antibacterial amount of an antibacterial component comprising one or more components selected from the group consisting of $C_7$–$C_{12}$ fatty acid monoglycerides, $C_6$–$C_{14}$ fatty alcohols, $C_{16}$–$C_{20}$ mono- or polyunsaturated fatty acids and monoglycerides thereof, $C_{16}$–$C_{20}$ mono- or polyunsaturated fatty alcohols, and ether and lysophosphatidylcholine derivatives of $C_4$–$C_{22}$ fatty acids.

9. A method of killing microorganisms in a microbe-containing medium which comprises contacting said medium with an antimicrobial effective amount of an antimicrobial component comprising one or more compounds selected from the group consisting of $C_7$–$C_{12}$ fatty acid monoglycerides, $C_6$–$C_{14}$ fatty alcohols, and ether and lysophosphatidylcholine derivatives of $C_4$–$C_{22}$ fatty acids.

10. The method of claim 9, wherein the antimicrobial component is added to the medium.

11. The method of claim 9, wherein the medium is transmitted to the antimicrobial component or a substrate containing said antimicrobial component.

12. The method of claim 9 wherein the antimicrobial component comprises one or more compounds selected from the group consisting of 1-O-decyl-sn-glycerol, 1-O-lauryl-sn-glycerol, 1-O-octyl-sn-glycerol, 1-O-oleyl-sn-glycerol, L-α-lysophosphatidylcholine caproyl, L-α-lysophosphatidylcholine decanoyl, and lysophosphatidylcholine lauroyl.

13. The method of claim 9, wherein the medium contains enveloped viruses.

14. The method of claim 9, wherein viral, bacterial or other microbial contaminants in products produced by procaryotes, protozoa, or eucaryotic cells, tissues, or organs or their derivatives in culture are inactivated.

15. The method of claim 9, wherein infectious agents in biologically active products isolated from living organisms are inactivated.

16. The method of claim 15, wherein viral contaminants in wound healing factor are inactivated.

17. A method for inactivating enveloped viruses in a medium containing enveloped viruses which comprises contacting said medium with an antiviral effective amount of a antiviral component comprising one or more compounds selected from the group consisting of $C_6$–$C_{14}$ fatty alcohols, and ether and lysophosphatidylcholine derivatives of $C_4$–$C_{22}$ fatty acids.

* * * * *